United States Patent [19]

Bernstein

[11] Patent Number: 4,927,813
[45] Date of Patent: May 22, 1990

[54] METHOD AND COMPOSITION FOR TREATING PEDICULOSIS CAPITIS

[76] Inventor: Joel E. Bernstein, 615 Brierhill Rd., Deerfield, Ill. 60015

[21] Appl. No.: 165,473

[22] Filed: Mar. 8, 1988

[51] Int. Cl.$^5$ .............. A61K 7/06; A61K 37/48; A01N 63/02
[52] U.S. Cl. .............. 514/65; 514/578; 514/730; 424/74; 424/94.6; 424/401; 424/405
[58] Field of Search ............ 514/65, 578, 730; 424/74, 94.6, 401, 405

[56] References Cited

U.S. PATENT DOCUMENTS 1,514,377  11/1924  Dow et al. .................. 514/730
3,083,136   3/1963  Levy ........................... 514/65

*Primary Examiner*—John Kight, III
*Assistant Examiner*—Nathan M. Nutter
*Attorney, Agent, or Firm*—Dressler, Goldsmith, Shore, Sutker & Milnamow, Ltd.

[57] ABSTRACT

A composition and method for removing head lice nits from a human are disclosed. The composition contains a therapeutically effective amount of formic acid in a pharmaceutically acceptable carrier. The composition is applied to the hair and scalp of a patient and maintained for a time period sufficient to dissolve the nit cement and provide detached nits. The hair and scalp are then washed or rinsed to remove the detached nits.

19 Claims, No Drawings

METHOD AND COMPOSITION FOR TREATING PEDICULOSIS CAPITIS

BACKGROUND OF THE INVENTION

The present application relates generally to the treatment of parasite infestations and, more particularly, to methods and composition to treat lice infections.

*Pediculosis capitis* (head lice) is an infestation of *Pediculosis humanus*, the human louse. This insect is transmitted to noninfected individuals through shared clothing and hairbrushes. Once present on the head, the adult female louse has a lifespan of about 25 days and lays up to 10 eggs each day which are attached to the hair shaft with a strong cement. Eggs hatch within 7–9 days producing more adult lice which continue the cycle. As the lice feed, they inject their digestive juices and fecal material into the skin and these "bites" cause pruritus.

In the past, chemical agents, including insecticides, have been used to treat pediculosis. These compounds include cholinesterase inhibitors such as neostigmine (Merch Index, Tenth Edition, entry no. 6311) or prostigmine (Merch Index Tenth Edition, entry no. 6311), and range from fairly toxic (thepyrethrins, Merch Index, Tenth Edition, entry no. 7865) to very toxic (lindane (Merch Index, Tenth Edition, entry no. 5329), malathion (Merch Index, Tenth Edition, entry no. 5522). All methods involve the exposure of the scalp and hair to these agents in shampoos or creams which are washed off relatively quickly.

While these current treatments are generally effective at killing the adult lice and eggs (nits), the dead nits remain firmly attached to the hairs after treatment. this is unsettling to the patient, as well a significant cosmetic problem. The only current means of removing dead nits is with a fine-toothed comb or forceps. These methods are time consuming and less than certain.

Formic acid, $CH_2O_2$, is an acid produced by ants through a distillation process. It can also be made by heating carbon monoxide and NaOH under pressure and decanting the resulting sodium formate with sulfuric acid ($H_2SO_4$). Formic acid is a colorless liquid that is irritating to the skin. It has, however, been used in cosmetics (0.05%–0.2%) as a preservative or an astringent.

It has been found, surprisingly, that formic acid is useful in the treatment of pediculosis in that concentrations of formic acid from about 1% to about 25% can be used to remove dead nits from hair without producing undue damage to hair or skin. This "nit removing" activity of formic acid can be observed and utilized clinically either by incorporating formic acid by itself into a shampoo or rinse for use after a pediculicide preparation or by incorporating formic acid into the shampoo, lotion, or cream containing the active pediculicide.

SUMMARY OF THE INVENTION

The present invention provides an improved method of and composition for the removal of pediculosis nits (eggs) from the hair of individuals with *Pediculosis capitis* (head lice). The method involves single or multiple applications of shampoos, rinses, creams, or lotions containing a constitutent selected for its efficiency in dissolving the cement that holds the nits in place either immediately following treatment with a chemical pediculicide or simultaneous with the use of chemical pediculicides.

DETAILED DESCRIPTION OF THE INVENTION

In the practice of this invention formic acid is incorporated into topical products suiable for application to the hair and scalp, then applied and removed by washing after 5 to 15 minutes of contact with the hair. Products suitable for application to the hair and scalp into which formic acid may be incorporated for this use in concentrations of from 1% to 25% includes shampoos, rinses, creams, gels, lotions and solutions. Concentrations of formic acid greater than 25% are very caustic and may cause severe damage to hair and scalp.

Although formic acid may be utilized successfully in connection of from 1% to 25% to remove nits, the preferred range which provides effecftive removal with minimal irritant effects is from 1% to 10%. Usually a single application to the hair, left for 5 to 25 minutes, and then removed by washing is sufficient to remove all or most nits. However, additional applications may be required to remove remaining nits. The following examples illustrate the present invention.

EXAMPLE 1

A 12 year old female with *Pediculosis capitis* utilized a 10% agueous solution of formic acid following shampooing of her hair with lindane, an insecticide used to kill head lice. The formic acid solution was worked into the hair and allowed to remain for 5 minutes, after which it was washed off in the shower. After drying and combing the hair, none of the over 50 nits that were present before treatment remained attached to the hair.

EXAMPLE 2

Formic acid was incorporated into a commercially available creme rinse to a concentration of about 1%. Three hairs with firmly attached nits were soaked in the formic acid containing rinse for 10 minutes in a glas plate. The three hairs were then rinsed in warm water and examined after air dyring in the light. None of the hairs had a nit attached following this procedure.

EXAMPLE 3

Solutions of 1%, 5% and 25% formic acid were prepared in water and 3 different sets of three hairs to which nits (previously treated with lindane) were firmly attached were exposed to each concentration for 5 minutes each. The hairs were then washed, air dried and examined. All three nits were successfully removed from the hairs treated with 5% and 25% formic acid. One of the hairs treated in this fashion with 1% formic acid still retained a nit, while th other two hairs were nit-free.

EXAMPLE 4

Solutions of 1%, 2.5%, 5% and 25% formic acid were patch tested on the back of a 42 year female. Solutions were painted on previously marked one such by one inch areas of the back and left in place for 30 minutes before being removed. No irritation was observed in the areas treated with 1% or 2,5% formic acid; a ± erythema was noted in the patch treated area with 5% solution; a 1+ erythema was noted in the area where 25% formic acid had been applied and the subject complained of stinging and itching at that site.

While it is not fully understood how the formic acid accomplishes this result, it is believed that the formic acid reacts with and fractures or dissolves the cement holding the nit to the hair shaft. It is expected that other compounds may have the same effect, and any such therapeutically effective compound which loosens the nits in concentrations which are non-irritating an nontoxic to the skin and scalp may be used in the practice of this inventin.

While the foregoing has presented specific emodiments of the present invention, it is to be understood that these embodiments have been presented by way of example only. It is expected that other will perceive and practice variations which, though differing from the foregoing, do not depart from the spirit and scope of the invention as described and claimed herein.

What is claimed is:

1. A method of treating a human patient having *Pediculosis capitis* by removing the nits from the patient's hair and scalp, said method comprising;

applying a composition containing a nit cement-dissolving amount of formic acid to the hair and scalp of said patient;

maintaining said formic acid on said hair and scalp for a time period sufficient to dissolve the cement attaching said nits to said hair and scalp to provide detached nits; and washing or rinsing said hair and scalp to remove said detached nits.

2. The method of claim 1, wherein said formic acid is dispersed in a pharmaceutically acceptable carrier and, thereafter, applied topically to said patent.

3. The method of clai 2 where said formic acid is present in said carrier in the range of from 1 to 25% by volume.

4. The method of claim 2, wherein sid pharmaceutically acceptable carrier is a shampoo, rinse, cream, gel, lotion or solution suitable for applicaton to the hair and scalp.

5. The method of claim 1 wherein said formic acid is maintained on said hair and scalp for about 5 to about 25 minutes.

6. The method of claim 1 including the further step of combing said washed or rinsed hair.

7. The method of claim 1 wherein said formic acid is present in said composition at about 1 to about 25 percent by volume, and said composition is maintained on said hair and scalp for about 5 to about 25 minutes.

8. A method of treating a human patient having *Pediculosis capitis* by killing lice and eggs and by removing nits from the patient's hair and scalp, said method comprising;

applying a topical composition containing a lice- and nit-killing amount of an active pediculicide and a nit cement-dissolving amount of formic acid to the hair and scalp of said patient;

maintaining said composition on said hair and scalp for a time period sufficient to dissolve the cement attaching said nits to said hair and scalp to provide detached nits; and washing or rinsing said hair and scalp to remove said detached nits.

9. The method of claim 8 wherein said formic acid is present in said composition at about 1 to about 25 percent by volume, and said composition is maintained on said hair and scalp for about 5 to about 25 minutes.

10. The method of claim 8 including the further step of combing said washed or rinsed hair.

11. The method of claim 8 wherein said composition contains about 1 to about 10 percent by volume of formic acid.

12. A topical composition effective in removing pediculosis nits, said composition comprising a pharmaceutically acceptable carrier containing a therapeutically effective amount of formic acid. d 13. The composition of claim 12 wherein the effective formula includes formic acid present in an amount not less than 1% by volume.

14. A topical compsition for killing lice and lice eggs, and for removing nits from the hair and scalp of a human patient, said composition comprising a lice- and nit-killing amount of a chemically active pediculicide and a nit cement-dissolving amount of a chemically active ingredient to dissolve the cement securing said nits to said patient's hair and scalp.

15. The composition of claim 14 wherein said pediculicide is lindane, a pyrethrin compound, or a cholinesterase inhibitor.

16. The composition of claim 15 wherein said cholinesterase inhibitor is neostigmine or prostigmine.

17. The composition of claim 14 wherein said chemically active ingredient is formic acid.

18. The composition of claim 15 wherein formic acid is present in an amount not less than 1% by volume.

19. The composition of claim 17 wherein said formic acid is present in said composition at about 1 to about 10 percent by volume.

* * * * *